(12) United States Patent
Frank

(10) Patent No.: US 12,690,819 B2
(45) Date of Patent: Jul. 28, 2026

(54) EARLY RECOGNITION OF CHANGE TO PATHOPHYSIOLOGIC STATE OF DYSGLYCEMIA

(71) Applicant: FRANK HEALTHCARE ADVISORS, LLC, Gainesville, FL (US)

(72) Inventor: Richard A Frank, Gainesville, FL (US)

(73) Assignee: Frank Healthcare Advisors, LLC, Gainesville, FL (US)

( * ) Notice: Subject to any disclaimer, the term of this patent is extended or adjusted under 35 U.S.C. 154(b) by 0 days.

(21) Appl. No.: 18/469,360

(22) Filed: Sep. 18, 2023

(65) Prior Publication Data

US 2025/0090103 A1     Mar. 20, 2025

(51) Int. Cl.
*A61B 5/00*          (2006.01)
*A61B 5/145*         (2006.01)
(Continued)

(52) U.S. Cl.
CPC ........ *A61B 5/7275* (2013.01); *A61B 5/14532* (2013.01); *G16H 10/60* (2018.01); *G16H 50/20* (2018.01); *G16H 50/50* (2018.01)

(58) Field of Classification Search
None
See application file for complete search history.

(56) References Cited

U.S. PATENT DOCUMENTS

| | | |
|---|---|---|
| 7,118,919 B2 | 10/2006 | Yatscoff et al. |
| 11,615,392 B2 | 3/2023 | Ilincic et al. |

(Continued)

FOREIGN PATENT DOCUMENTS

| | | |
|---|---|---|
| WO | 2021011697 A1 | 1/2021 |
| WO | 2021040878 A1 | 3/2021 |
| WO | 2023034542 A1 | 3/2023 |

OTHER PUBLICATIONS

Classification and Diagnosis of Diabetes: Standards of Care in Diabetes—2023, Diabetes Care vol. 46, Supplement 1, Jan. 2023, https://doi.org/10.2337/dc23-S002.

(Continued)

*Primary Examiner* — Tse W Chen
*Assistant Examiner* — Martin Nathan Ortega
(74) *Attorney, Agent, or Firm* — Sheppard Mullin Richter & Hampton LLP

(57)          ABSTRACT

Conditions of pathophysiologic dysglycemia, associated with type 1 diabetes, can be detected early, including in children. Glycemia data is collected by continuous glucose monitoring devices connected to a cloud server. The server learns person-specific patterns of glycemia and trains a model accordingly, which may serve as a baseline for comparison or as the basis for prediction of future patterns. Such models are conditioned by risk factors and various concurrent activities such as exercise and consumption of sugars. Person-specific models trained at different time periods give different simulated patterns of glycemia. Deviations between the simulated patterns, or between the predicted and actual patterns, can indicate progression of pathophysiologic dysglycemia and type 1 diabetes. These models and comparisons can be further interpreted by the software to result in a reported recommendation for additional diagnostic testing or a reported conclusion of diagnosis and recommendation of preventative intervention.

24 Claims, 11 Drawing Sheets

(51) Int. Cl.

| | |
|---|---|
| *G16H 10/60* | (2018.01) |
| *G16H 50/20* | (2018.01) |
| *G16H 50/50* | (2018.01) |

(56) References Cited

U.S. PATENT DOCUMENTS

| | | | | |
|---|---|---|---|---|
| 2003/0044993 | A1* | 3/2003 | Yatscoff | A61K 51/1206 |
| | | | | 435/14 |
| 2009/0216460 | A1 | 8/2009 | Abensour et al. | |
| 2010/0261987 | A1* | 10/2010 | Kamath | A61B 5/744 |
| | | | | 600/365 |
| 2012/0059673 | A1 | 3/2012 | Cohen et al. | |
| 2012/0328594 | A1* | 12/2012 | McKenna | G01N 33/6893 |
| | | | | 424/94.4 |
| 2014/0148867 | A1* | 5/2014 | Zielinski | A61B 5/085 |
| | | | | 607/3 |
| 2015/0289821 | A1 | 10/2015 | Rack-Gomer et al. | |
| 2018/0160985 | A1 | 6/2018 | Willis | |
| 2020/0118647 | A1 | 4/2020 | Zhang et al. | |
| 2020/0227166 | A1* | 7/2020 | Rose | G16H 10/40 |
| 2020/0227170 | A1* | 7/2020 | Shvets | G16H 20/17 |
| 2021/0050089 | A1* | 2/2021 | Mohammed | A61B 5/7267 |
| 2021/0077719 | A1 | 3/2021 | Cardinali et al. | |
| 2021/0183508 | A1* | 6/2021 | Parker | G06N 3/08 |
| 2021/0187197 | A1 | 6/2021 | Zade et al. | |
| 2021/0338116 | A1 | 11/2021 | Acciaroli et al. | |
| 2022/0062545 | A1* | 3/2022 | Zade | A61K 38/28 |
| 2022/0142521 | A1 | 5/2022 | Russo | |
| 2022/0202320 | A1* | 6/2022 | Diener | A61B 5/14532 |
| 2022/0358561 | A1* | 11/2022 | Kim | A61B 5/7275 |
| 2022/0379029 | A1* | 12/2022 | Zade | A61M 5/16804 |
| 2023/0129902 | A1* | 4/2023 | Park | G16H 50/50 |
| | | | | 705/2 |
| 2024/0074708 | A1* | 3/2024 | Jang | A61B 5/7275 |

OTHER PUBLICATIONS

Martin Tauschmann, et al., ISPAD Clinical Practice Consensus Guidelines 2022: Diabetes technologies: Glucose monitoring, Pediatric Diabetes, Nov. 5, 2022; 23:1390-1405, DOI: 10.1111/pedi.13451.

Olena Litvinova, et al., Patent analysis of digital sensors for continuous glucose monitoring, Frontiers in Public Health, Aug. 9, 2023, DOI 10.3389/fpubh.2023.1205903.

\* cited by examiner

21

| Risk factor | Possible values |
|---|---|
| Antibody (Aby) | +, -, unknown |
| Family history | +, -, unknown |
| OGTT | milligrams per deciliter (mg/dL), unknown |
| HLA-DR3 | normal, mutated, unknown |
| HLA-DR4 | normal, mutated, unknown |
| HLA-DR7 | normal, mutated, unknown |
| HLA-DR9 | normal, mutated, unknown |
| Other genes… | normal, mutated, unknown |
| Age | [integer] |
| Gender | male, female |
| Zip code | [risk table lookup], unknown |
| … | … |

FIG. 7 historical
glucose monitoring data real-time
glucose monitoring data

<u>81</u>

Learn a person-specific model
of patterns parameters

<u>82</u> model prediction

<u>83</u> compute a deviation of
subsequent glucose monitoring
data from a prediction based on
the model device configuration message

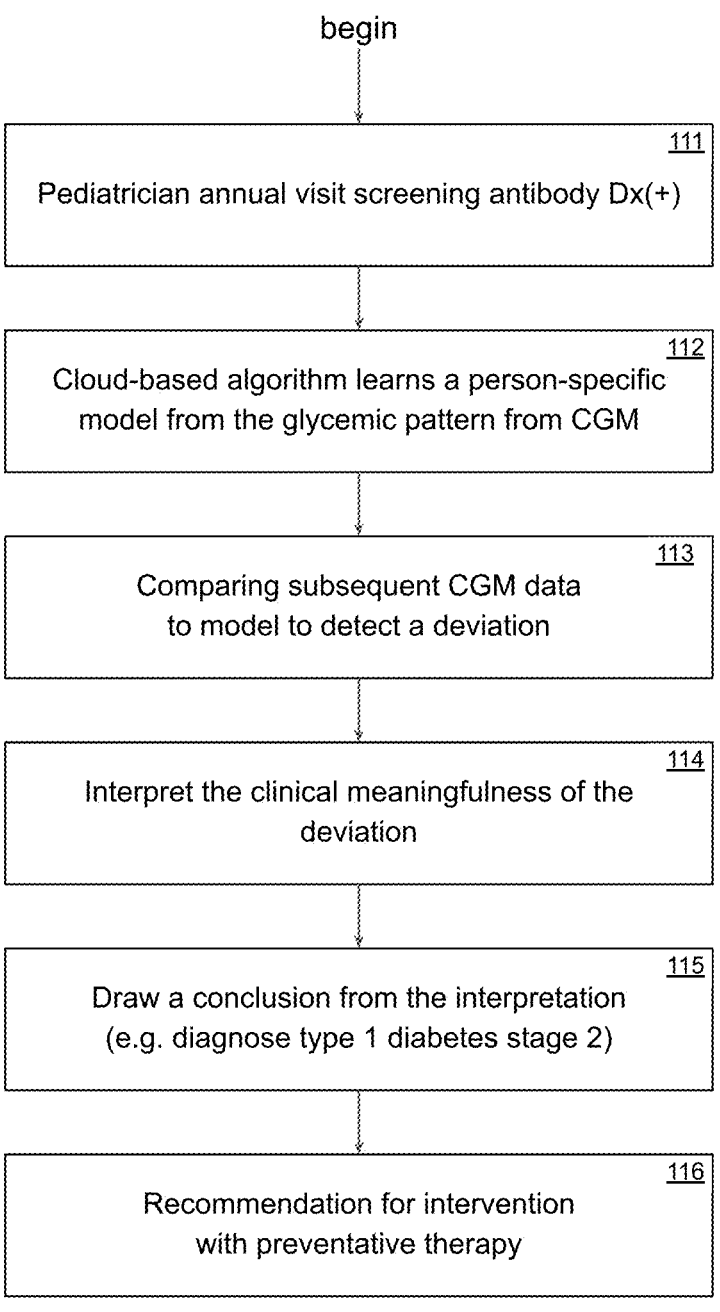

begin

111
Pediatrician annual visit screening antibody Dx(+)

112
Cloud-based algorithm learns a person-specific
model from the glycemic pattern from CGM 113
Comparing subsequent CGM data
to model to detect a deviation 114
Interpret the clinical meaningfulness of the
deviation 115
Draw a conclusion from the interpretation
(e.g. diagnose type 1 diabetes stage 2)

116
Recommendation for intervention
with preventative therapy

FIG. 11

EARLY RECOGNITION OF CHANGE TO PATHOPHYSIOLOGIC STATE OF DYSGLYCEMIA

SUMMARY

We describe, herein, methods, devices, and computer programs for recognizing pathophysiologic dysglycemia early. Doing so allows diagnosis and appropriate treatments for type 1 diabetes before it can cause dangerous incidents such as diabetic ketoacidosis. Approaches can include local and cloud-based processing using various combinations of mobile handsets, glucose monitoring devices, servers, electronic health records, and clinical decision support platforms.

Continuous glucose monitoring data reveals patterns of glycemia, which vary from one person to another and are affected by meals and snacks, exercise and sleep, and other factors. These patterns can be identified for numerous days to train a person-specific model. The model can take in a real-time pattern or time of day information or additional related information such as meals, exercise, and sleep.

Identifying the magnitude and changes over time of deviations between models of glycemia patterns within a person over certain time periods indicates stability or failure to maintain the pattern of glycemia predicted by the initial models, indicating the onset of, or worsening of, pathophysiologic dysglycemia. By accurately identifying both onset of dysglycemia and trends towards pathophysiologic dysglycemia, new standards of care and patient care pathways become possible that can avoid dangerous events and provide better control of diabetes, or intervention to prevent or delay progression to insulin dependence.

DESCRIPTION OF DRAWINGS

FIG. 7 is a table of types of values for examples of risk factors on which a predictive model can be conditional.

FIG. 11 shows an example of a standard of care pathway using detection of deviation, interpretation, and a conclusion of diagnosis and recommended intervention.

DETAILED DESCRIPTION

Figure 1A:
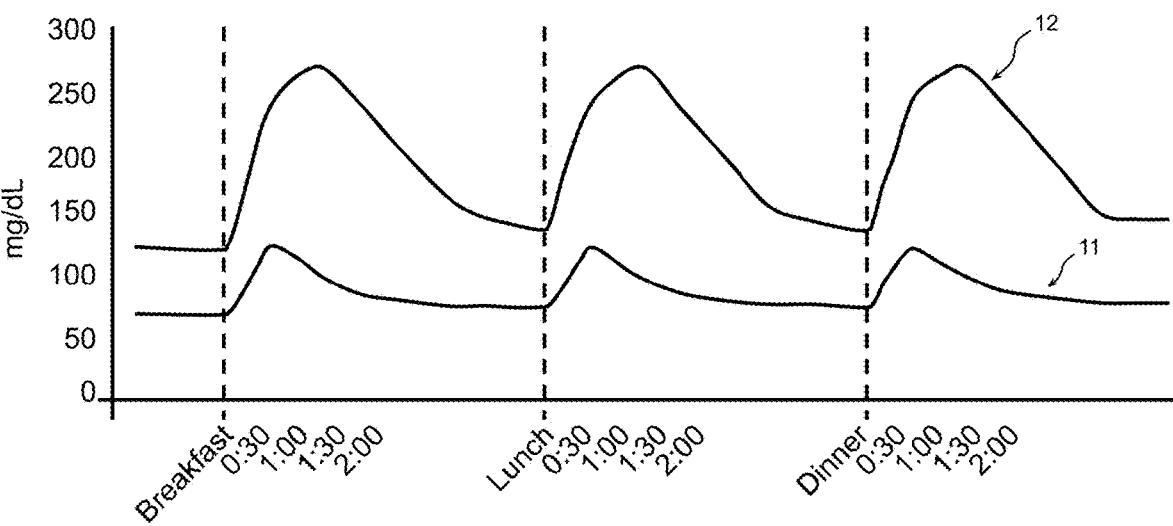
FIG. 1A shows a chart of a scenario of an individual person's glucose concentration variation throughout a day with three meals.

Using current healthcare technology under standard of care clinical pathways, children with diabetes often suffer life-threatening diabetic ketoacidosis (DKA) as their initial symptom.

Type 1 diabetes is a chronic metabolic disorder characterized by insufficient insulin production by the pancreas. Insulin promotes the absorption of glucose from the blood into cells of the body. A lack of insulin causes the glucose homeostasis to change from a normal state (euglycemia) to an abnormal state (dysglycemia). One abnormal state is hypoglycemia, for example during fasting or exercise, which can lead to unconsciousness. Hypoglycemia is commonly defined as a blood sugar concentration lower than 70 milligrams per deciliter (mg/dL), whereas hyperglycemia is commonly defined as a blood sugar concentration higher than 200 mg/dL. Another abnormal state is hyperglycemia, which puts the person at risk of a range of long-term sequelae, or ketoacidosis due to metabolism of fat in lieu of glucose, which can induce coma. Type 1 diabetes can lead to ketoacidosis, heart disease, neuropathy, nephropathy, retinopathy, foot damage, skin infections, pregnancy complications, among other complications. Current treatment methods involve lifestyle modifications, insulin therapy, medications, artificial pancreas (a closed-loop insulin pump), beta cell replacement therapies, and others. None of these approaches are fully effective, and most have serious side effects. There is no known cure for type 1 diabetes.

However, recently the United States Food and Drug Administration (FDA) approved a therapy that can delay the onset of insulin-dependence, but only if risk factors can be detected early, for example at Stage 2. Some implementations of analysis of patterns in glycemia using artificial intelligence (AICGM) may provide early detection of type 1 diabetes. This can have a clinical advantage in that early detection enables early intervention, avoiding DKA and other complications by preserving the person's normal pancreatic function of insulin secretion. Indeed, dysglycemia is a criterion for Stage 2, and is also one of the criteria used by physicians in prescribing the preventative therapy which can delay onset. Currently, dysglycemia is determined from an Oral Glucose Tolerance Test (OGTT). OGTT requires a clinic visit and at least two blood draws hours apart. That process is inconvenient and time-consuming for patients and creates a slower and therefore more expensive workflow for clinics. It is administered at long intervals and misses the earliest opportunity for intervention to preserve insulin secretion.

AICGM can determine which children should be tested using the OGTT. In some cases, AICGM can enable a change in the standard of care by replacing OGTT, which is cumbersome and episodic. Patients, especially in the general population, often skip tests. Under any circumstances, OGTT only detects the instantaneous state of glycemia. If the interval of testing is not coincident with the early periods of dysglycemia ("interval incidence"), the patient may suffer complications of diabetes shortly after the last OGTT and months or years before the next one is scheduled. Methods disclosed herein can enable early detection, diagnosis, and intervention to delay the onset of insulin dependence.

AICGM, in some cases, can supplant the conventional step of referring patients to an OGTT test. In such a case, a patient can be referred directly to a course of treatment. Such a use could be manifest in Clinical Practice Guidelines and United States Preventive Services Task Force (USPSTF) screening recommendations. The Juvenile Diabetes Research Foundation advocates screening the general pediatric population for the risk of diabetes. AICGM can be instrumental in optimizing such screening by providing the earliest detection of dysglycemia warranting intervention to delay the onset of insulin dependence.

Type 1 diabetes can be caused by an autoimmune attack on pancreatic beta cells. Beta cells produce insulin for regulating blood glycemia. Beta cells also produce glutamic acid decarboxylase (GAD). Type 1 diabetes caused by an autoimmune attack that kills beta cells occurs when the immune cells respond to GAD as an antigen. A blood test that detects immune cell response to GAD indicates that the person is, so called, antibody positive (Aby+). Otherwise, the person is antibody negative (Aby−). There are 3 other antibodies which can contribute to the autoimmune attack on insulin-producing beta cells. The detection of dysglycemia, as described herein, in a person with any two of these four antibodies, is diagnostic of Stage 2 diabetes and warrants intervention with the preventative therapy.

A person who is known to be Aby+ has a different prior risk of having type 1 diabetes than someone who is Aby−. Similarly, a person with a 1st degree relative who is diabetic also has a different risk than someone in the general population. There also are other genetic risk factors.

The detection of glycemic patterns differs. It also has different implications for the need for intervention. A person who is Aby−, for example from the general pediatric population or from the general pediatric population with known genetic risk factors such as HLA, would be euglycemic and therefore the change from that state is generally easier to detect. Those who are Aby+ may already be experiencing early, mild dysglycemia, perhaps not even detected by OGTT, but would represent a different baseline than those who are Aby−.

Preventative intervention is distinct from a therapeutic. The drug Tzield is like a vaccine, preventing the immuno-logic destruction of insulin-producing beta cells, thereby delaying insulin dependence. An older approach is thera-peutic. Typically it is prescription of exogenous insulin in compensation for the patient's pathophysiologic insuffi-ciency which results from prolonged autoimmune-mediated destruction of insulin-producing beta cells and, hence, insu-lin dependence.

Data Variations

FIG. 1A shows a chart of blood glucose [glycemia] over time. Meal times are marked, followed by hours and minutes immediately following meals. The first curve 11 on the chart shows a normal, healthy fluctuation of blood glycemia through the day. It fluctuates between about 70 and 120 mg/dL with peaks very shortly after meals and rapid decays. The second curve 12 shows the blood glycemia through the day for a person with hyperglycemia which is typical of untreated insulin deficiency. It fluctuates between 120 and 270 mg/dL. Peaks occur somewhat later than normal. Peaks are also a lot higher and the minimum level after decay is also higher than a normal minimum.

Any particular person will have, on different days, dif-ferent patterns of blood glycemia. Sometimes higher overall, sometimes with larger variations in level, sometimes with faster or slower rates of increase and decrease. The varia-tions in patterns are affected by what time of day the person eats, what food the person eats, how much they move around [ranging from strenuous exercise to sleep], what their heart rate pattern is, and so forth.

Figure 1B:
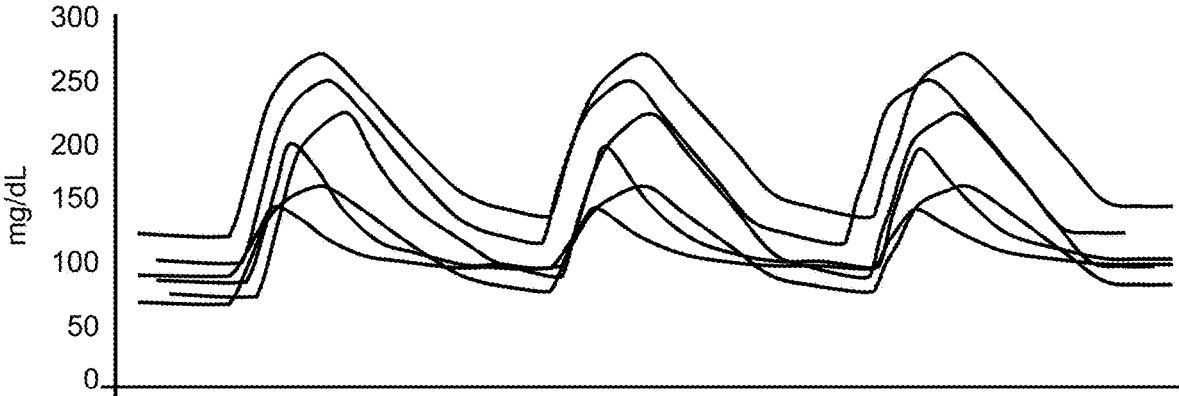
FIG. 1B shows a chart of a scenario of a multiplicity of glucose concentration variations throughout multiple days for an individual person.

FIG. 1B shows a chart of glucose measurements across a full day for several days. Whether they have pathologic dysglycemia or not, to what degree, and whether the con-dition is deteriorating is essentially impossible to discern from the data by direct human observation.

However, a model of an expected pattern of glycemia can be created by analysis of a large number of patterns using machine learning. Such a model can be implemented, for example, as a neural network or other model having param-eters that give specifically calculated weights to input data. Some such neural networks use recurrence. Simple recur-rence is useful for representing instantaneous changes in glycemia from one time sample to the next.

A more complex form of recurrence is a long short-term memory (LSTM). This can be useful to represent the fact that glucose is, in essence, stored in the blood. The size of the body and organs can affect the storage. So, the rate of change of glycemia can have latencies based on the amount of stored glucose. The storage can be modeled by a LSTM.

One or more models can be trained to predict one or more of the likelihood of type 1 diabetes, severity of episodes of dysglycemia, maximum glycemia, and responsiveness to acute or ongoing treatments. Methods of training such models will be described below.

Example Devices

Many sufferers of type 1 diabetes use glucose monitoring devices. Glycemia can be determined usings assays or electronic sensors. Glycemia can be measured directly or estimated by secondary indications through analysis of blood, intracellular fluids, interstitial fluids (ISF), tears, saliva, urine, sweat, and other fluids inside or exuded from the body. Various types of glucose monitoring devices can be assistive, augmentative, or autonomous.

Assistive devices can use local or cloud-based algorithmic detection and alerting of either or both of the subject person and a qualified healthcare professional (QHP) to review the glycemia data and consider whether additional diagnostic testing, such as antibody testing or oral glucose tolerance testing based on the person's trend over time from a state of euglycemia toward a state of dysglycemia detected in pat-terns of continuous glucose monitoring data or a model of such.

Augmentative devices can use local or cloud-based algo-rithmic quantification as an element of diagnosis and alert-ing either or both of the subject person and a QHP of an Aby+ person's transition over time from a state of eugly-cemia to a state of dysglycemia based on patterns in con-tinuous glucose monitoring data or a model of such.

Autonomous devices can use local or cloud-based algo-rithmic diagnosis and recommendation to a QHP for pre-ventative therapeutic intervention by taking into account the antibody status [Aby+ or Aby−] of the subject person and their transition over time from a state of euglycemia to a state of dysglycemia based on patterns in continuous glucose monitoring data or a model of such.

One type of device is based on a paper-based colorimetric lateral flow assay for measuring glucose from a drop of blood. Some such assays can be read by electronic devices, and some such electronic devices are connected to the internet and thereby able to upload results to a cloud server with personal data or other electronic health records.

Figure 2:
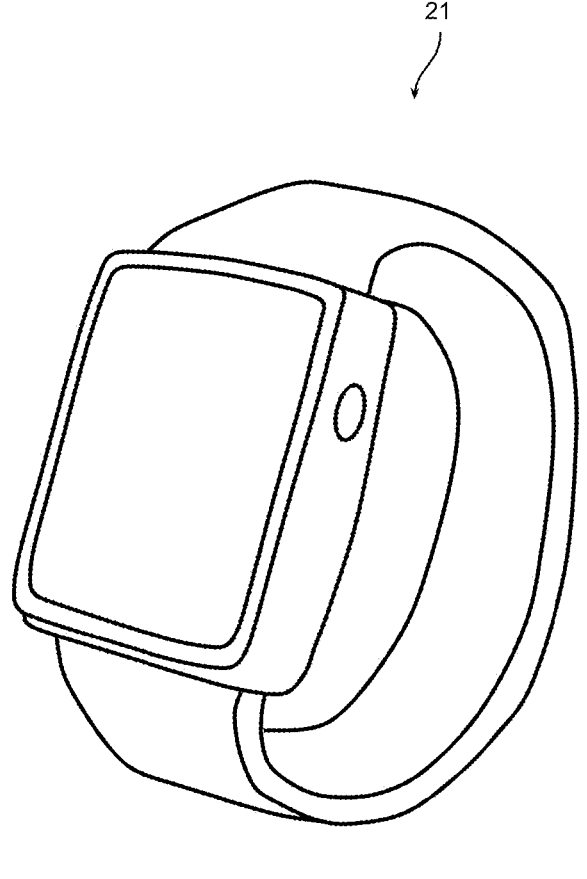
FIG. 2 shows an example of a continuous glucose monitor that fits on a person's wrist.

FIG. 2 shows another type of monitor. It is a smartwatch 21, worn on the wrists, that estimates glycemia without puncturing the skin (non-invasive monitoring). This can be performed in multiple ways, one of which is to emit light into the skin and measure the intensity of light reflected back. Some such smartwatches connect to smartphones or other devices that are connected to the internet and can upload glucose monitoring data to a cloud server. Some smartwatches connect directly to the internet through a wireless communication network such as 5G or WiFi.

Figure 3:
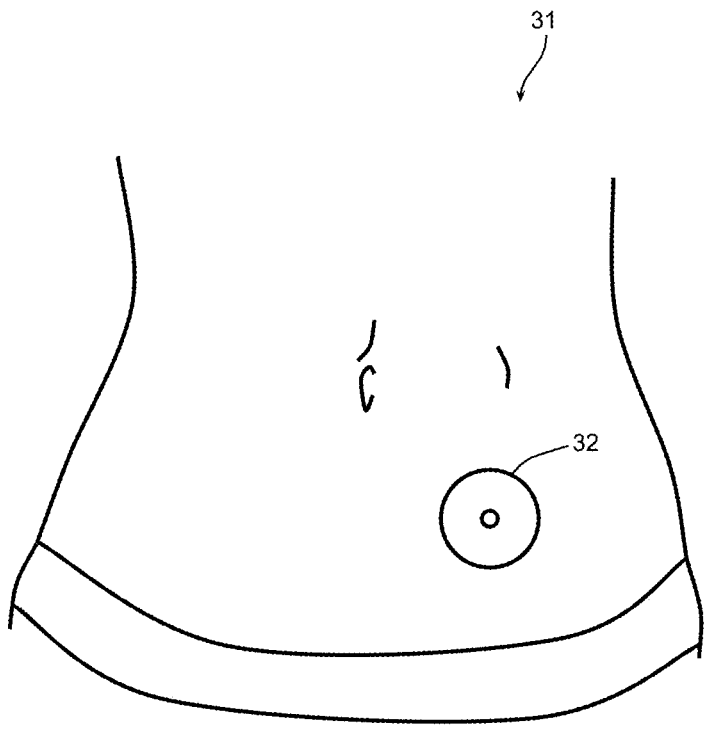
FIG. 3 shows an example of a continuous glucose monitor that sticks to the skin and can be worn under clothing.

FIG. 3. shows another type of monitor. It is one implanted under the skin of a person's abdomen 31. Data from the monitor is read by a transmitter 32, visible outside of the skin. It can measure glycemia in interstitial fluid and provide the measurement data to an electronic reader device wirelessly using a protocol such as near-field communication (NFC). Some such readers are connected to the internet and can upload data to the cloud.

Figure 4:
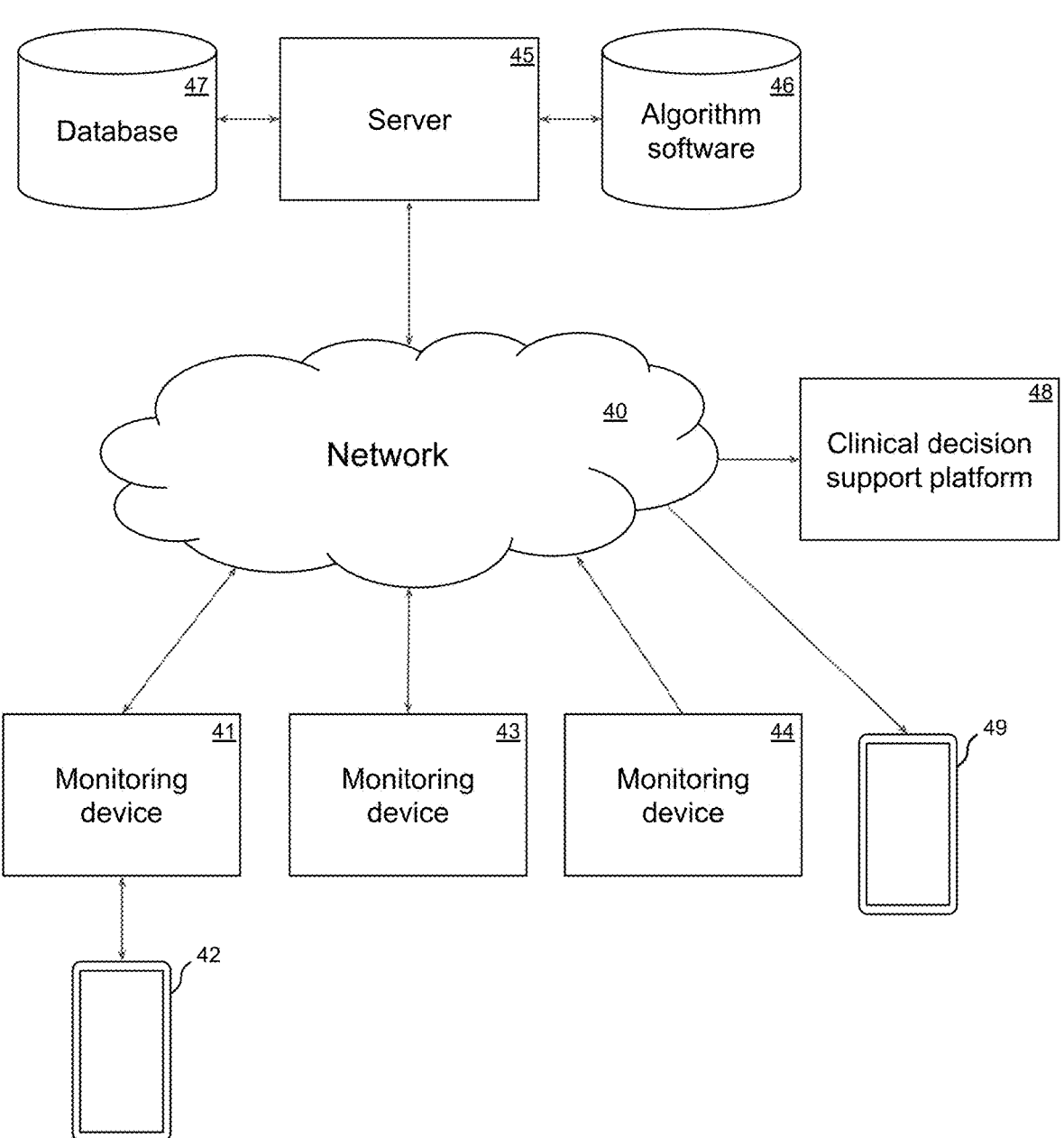
FIG. 4 is a diagram of examples of connected devices connectivity.

FIG. 4 shows a block diagram of a system for monitoring people using devices connected through a network 40. The network might be a local area network, such as one within a hospital, or the internet. A first monitoring device 41 monitors a first person. It is controlled by and provides data to a mobile device 42. Smartphones, tablet computers, home digital assistant devices, and healthcare provider operated devices are some examples. A second monitoring device 43 monitors a person. It could be the same or a different person. The second monitoring device 43 includes built-in information collection and storage capabilities and one or more of display and alert capabilities. Smartwatches, health rings, and clip-on monitors are examples. A third monitoring device 44 also monitors a person. It has no local user interface. It simply takes measurements and uploads them through the network 40.

The three monitoring devices communicate through the network 40 to a server 45. The server includes one or more processors such as a central processing unit and graphics processing unit. The server also includes storage such as a dynamic random access memory (DRAM) to store program code for the processors and data used for processing. The server 45 reads algorithm software instructions from a non-volatile storage device such as a magnetic hard disk drive or one or more Flash random access memory (RAM) chips. The server 45 executes the algorithm software, which accesses data from a hard drive or Flash RAM storage device 47. In different implementations, the database 47 and algorithm software 46 are stored in either the same or different data storage devices.

Various implementations of the server 45, algorithm software storage 46, and database 47 house those components for example, in multi-application data centers or within the buildings of an organization such as a hospital or electronic health record (EHR) provider. The physical location of the storage, in some implementations, is intentionally within the same politically geographically controlled region as the people with the monitoring devices reside.

A common way to upload or download data from devices to cloud servers or from cloud servers to a clinical decision support platform, such as one run by an EHR company, or a "dashboard" in a QHP's office, is by making requests through a web API.

The server 45 receives measurements and other data from the monitoring devices. It processes the data to identify monitoring devices that have measured a state of dysglycemia. In some implementations, the state of glycemia that characterize dysglycemia are person-specific and therefore implemented as conditional on personal data stored in the database 47.

In some implementations, the server 45 sends to a clinical decision support platform 48 one or more of alerts, measurements, patterns in measurements, patterns, and other information learned from measurements by monitoring devices. Some such platforms provide dashboards for periodic review and real-time alerts to physicians. When the server detects, for example, a person in dysglycemia, it can send an alert to a physician through the clinical decision support platform 48. Some examples of such a device are a computer in a doctor's office, a SMS pager, a smartphone or tablet computer app, or an email server. The physician alert device can inform a physician, in various implementations, of the identity of a patient in dysglycemia, the fact that they are in such a state, a chart of their recent glycemia prior to entering dysglycemia, and information for contacting the patient. Physician alert devices, in various settings, can be operated by physicians, nurses, hospital information technology (IT) services, or EHR providers.

In some implementations, the server 45, upon recognizing that a person is in dysglycemia, can send the same or similar information as provided to a physician alert system 48 to a mobile device used by a person or their family member. For example, monitor device 44 only provides data to the server 45, not to the person. That monitoring device 44 might be used by a child. The result of the server processing the data can be sent as output to a mobile device 49, such as a smartphone used by the child's parent or caretaker. In such a use case, the child's parent or caretaker might use the alert to provide a rapid intervention to the child.

Another type of monitor is a wrist watch that estimates glycemia without puncturing the skin (non-invasive monitoring). That can be performed in multiple ways, one of which is to emit light into the skin and measure the intensity of light reflected back. Some such smartwatches connect to smartphones or other devices that are connected to the internet and can upload glucose monitoring data to a cloud server. Some smartwatches connect directly to the internet through a wireless communication network such as 5G or WiFi.

Another type of monitor is one implanted under the skin. It can measure glycemia in interstitial fluid and provide the measurement data to an electronic reader device wirelessly using a protocol such as near-field communication (NFC). Some such readers are connected to the internet and can upload data to the cloud.

Whether connected to the cloud or not, glucose monitoring assays, devices, and other ways of measuring glycemia can provide personal health data if sampled with a frequency higher than the frequency of transitions between euglycemia to dysglycemia in blood glycemia. At least 2× higher frequency is ideal due to the Shannon theorem, but higher frequencies are generally better. Indeed, to detect a trend in the pattern of glycemia, whether directly from patterns in the data or patterns from a model learned from the data, would require a much richer database, ie, with many more frequent measurements. Despite the sampling frequency and type of device, such approaches are known as continuous glucose monitoring (CGM).

The measurements needed to detect changes in glycemia can be captured using a CGM device. They could also be captured by other types of devices that provide a stream of frequent measurements with high enough sampling frequency to recognize variations that can predict unexpected changes in glycemia. For example, it would be necessary to detect an abnormally rapid rate of rise in blood glucose after a carbohydrate load, due to the slower response of the beta cells to secrete insulin.

Pattern Analysis

Whether connected to the cloud or processed locally, glucose monitoring assays, devices, and other ways of measuring glycemia can provide valuable personal health data if sampled with a frequency higher than the frequency of transitions between euglycemia to dysglycemia in blood glycemia. At least 2× higher frequency is ideal due to the Shannon theorem, but higher frequencies are generally better. Sampling once every 15 minutes is appropriate for some applications. Once every 5 minutes is appropriate for some applications. Other more or less frequent sampling periods are also appropriate for some applications.

It is possible to store a sequence of measurements taken with sufficient frequency over a period of time in which a person's pattern of glycemia fluctuates on at least several occasions between states of euglycemia and dysglycemia. It is also possible to learn a model from this data.

Having this data enables pattern analysis. Analyzing patterns in real time (in contrast to retrospective analysis) can be used with continuous glucose monitoring (CGM).

In the example system of FIG. 4, the server 45 can detect and monitor patterns in the measurements of each person's glycemia. The server, in some implementations, receives other real-time measurements in conjunction with glycemia measurements. Some examples are heart pulse rate, movement such as step rate, location and speed, sweat level, blood oxygen concentration, and neural activity. Cross correlation between patterns of different types of measurements can condition the calculation of pathophysiologic dysglycemia. A low level of cross correlation (a) between a recent and baseline measurement, (b) between a recent and statistically modeled predicted pattern, (c) between a statistical model of recent patterns and a baseline, or (d) between a statistical model of recent patterns and a statistical model of past patterns can indicate a likely change in pathophysiologic state.

Figure 5:
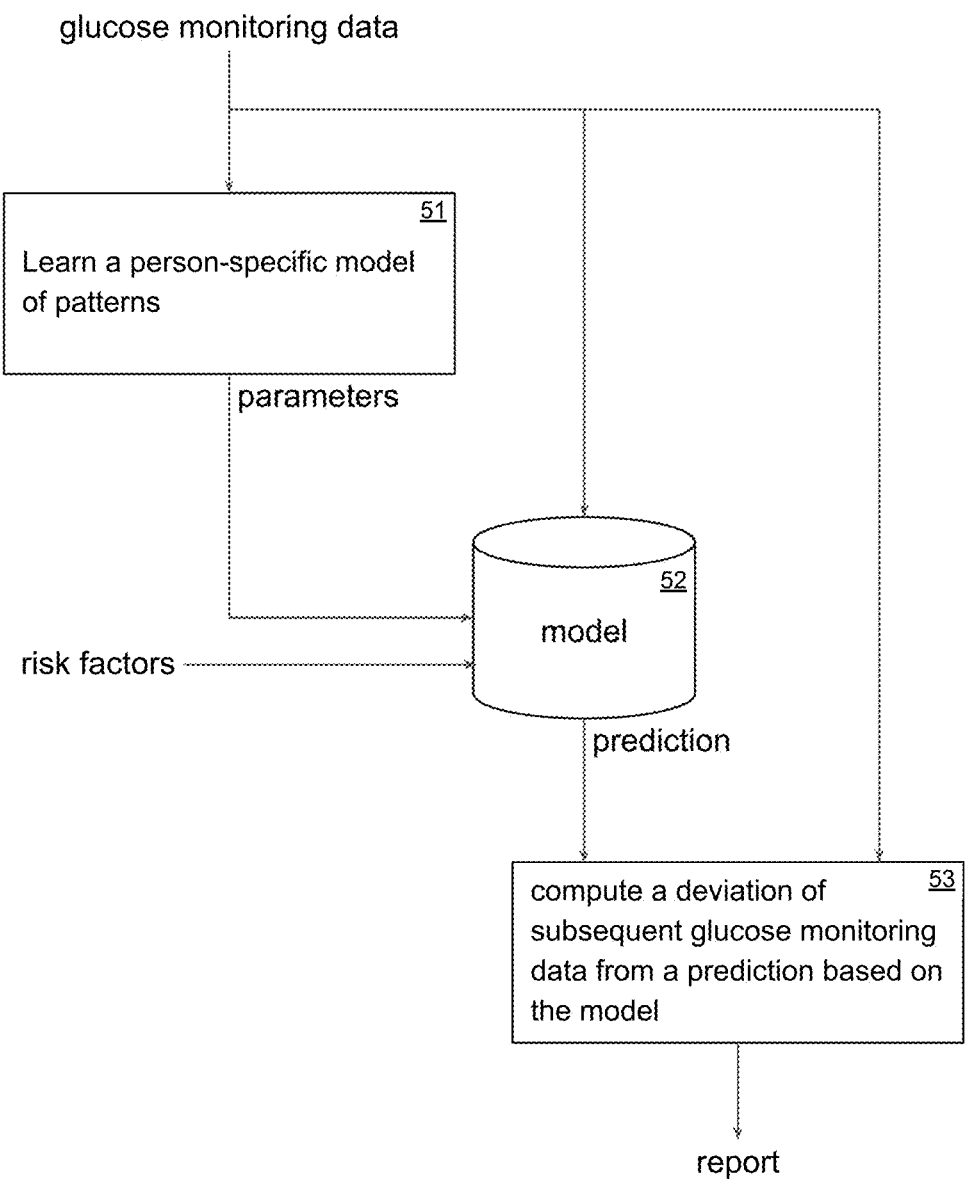
FIG. 5 is a diagram of an example of a method for reporting pathophysiologic dysglycemia.

FIG. 5 is a diagram of an example of a method for reporting a trend toward or onset of pathophysiologic dysglycemia. It begins with obtaining glucose monitoring data for a person. In various implementations, glucose monitoring data may be obtained from an EHR system, a device vendor's cloud server, Apple Health or Google Fit, directly from the computer memory within a device, or other sources.

A machine learning process 51 is applied to the data. This generates parameters for a model 52. The model 52 takes in a specified time of day and, from that, can infer a pattern of glycemia. In some implementations, the parameters are weights for a neural network. In some implementations, they are inputs to a formula. In some implementations, the model 52 also takes, as input, one or more risk factors specific to the person. Examples of risk factors are the person's family history of diabetes, whether they have tested positive for antibodies, and how many, and when, and whether they have genetic mutations frequently associated with diabetes.

The model 52 can take in glucose monitoring data from a different (generally later) time period and, in some implementations, additional data, to predict a pattern of glycemia. In various implementations, the pattern can be daily fluctuations, peaks immediately after meals, or aggregate fluctuations. The prediction is a process of inference by the machine learned model 52.

The model 52 outputs a predicted pattern of glycemia over a range of time. The method compares the prediction to actual glucose monitoring data received subsequently to training the model 52. The comparison is used to compute a deviation 53 of the actual from the predicted pattern. Computing the deviation can include either or both of (a) computing a difference in amplitude between the predicted and measured glycemia data and (b) computing a difference in rate of change between the predicted and measured glycemia data. The deviation may be reported directly to a QHP or their patient or patient's caretaker. Alternatively or additionally, the deviations can be translated to an estimated probability of certain outcomes.

For example, in various implementations, the resulting report can indicate a probability of the person testing positive in an OGTT test, the probability of a clinical diagnosis of pathophysiologic dysglycemia, the probability of a diagnosis of type 1 diabetes in stage 2, a probability of an event of ketoacidosis, and probabilities of other events or diagnoses. In various implementations, a cloud server automatically transmits the report over the internet to one or more of a remote EHR database, a physician's dashboard, or an app on a user's mobile device.

Figure 6:
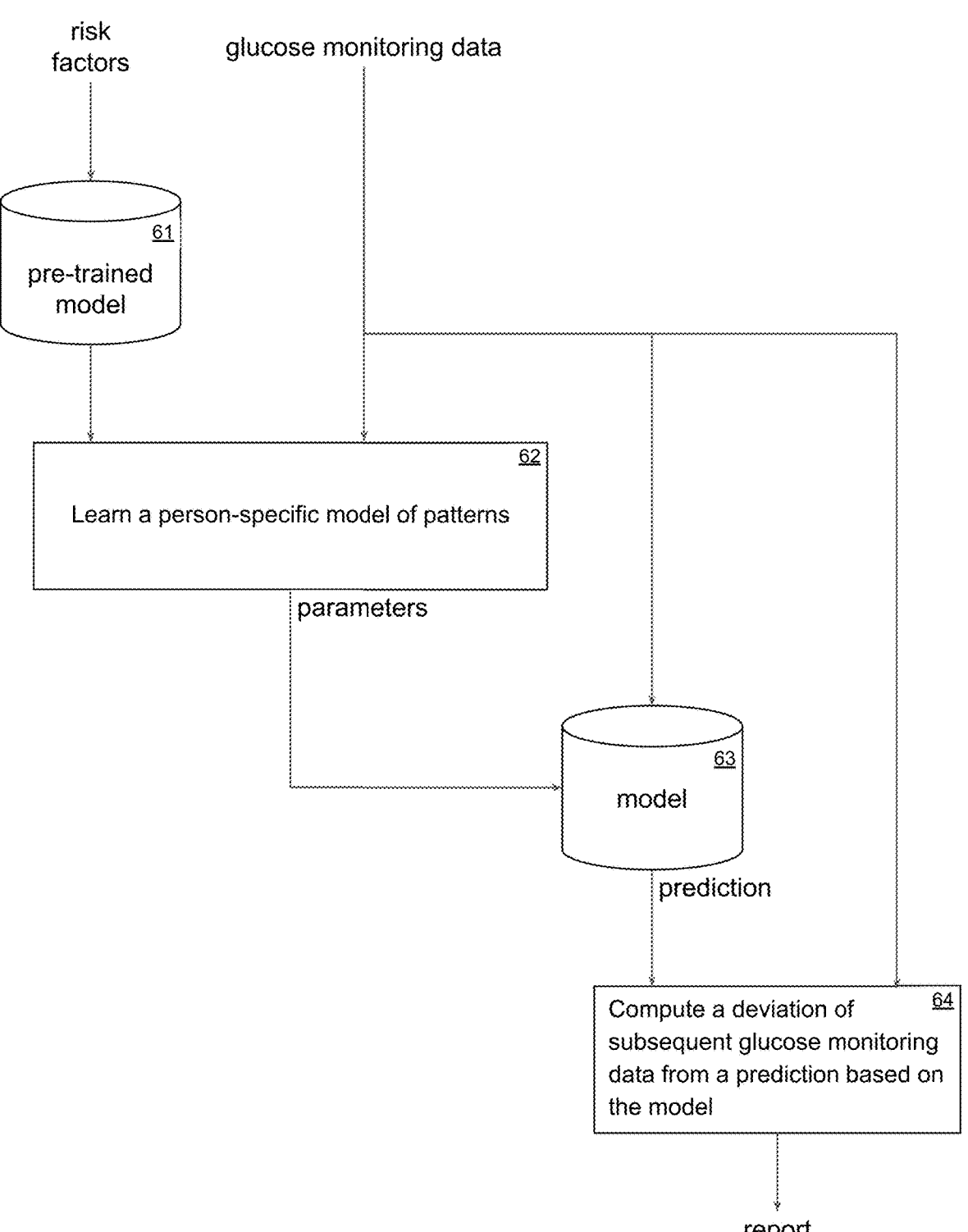
FIG. 6 is a diagram of an example of a method for reporting pathophysiologic dysglycemia.

FIG. 6 is a diagram of another example of a method for reporting pathophysiologic dysglycemia. It uses a pre-trained model 61 of patterns of glycemia, the model being conditioned on risk factors such as the ones described above. The pre-trained model 61 is used with person-specific glucose monitoring data for a process of fine tuning 62 to determine model parameters. These are used to create a model 63 of patterns of glycemia for the person. The model can take, as input, measured patterns of glycemia and, in some implementations, corresponding additional data.

The model 63 outputs predicted patterns of glycemia. The computation of the prediction is a method of inference using the machine learned model 63. As in the process of FIG. 5, the predicted patterns can be compared to patterns in actual glucose monitoring data in a further step 64 to produce a report. The report, in various embodiments, can include the types of probabilistic predictions described above.

The two example methods described above can, optionally, use risk factors to condition models of glycemia. FIG. 7 is a table of examples of risk factors and the data types of values for each risk factor shown. For example, antibody test results and family history can either be positive, negative, or unknown. In the case of OGTT test results as a risk factor, the input can be a number representing a level in units of, for example, milligrams per deciliter (mg/dL) or unknown. A number of mg/dL can be represented as a model input with, for example, an integer or floating point number.

Like antibody status and family history, genetic biomarkers can have three states of being normal (no mutation from the common human genome), mutated, or unknown. Genetic mutations can be detected by gene sequencing of the person being tested. In general, if any base pair of a necessary gene has a mutation, the protein for which it codes will be completely ineffective, and the protein that is normally coded at the location of that gene in the human genome will not be produced.

Another example risk factor is age, which can be represented with an integer number. Another example is gender as determined by the presence or absence of a human Y chromosome, which can be expressed as a single binary bit. Another example risk factor is zip code, which is a sequence of characters (5 numbers in the US, 6 numbers and letters in many other countries). The zip code can be used as a key into a demographic lookup table of probabilities of various diagnoses and outcomes.

Examples of models described herein that are conditional on risk factors can be designed or learned through machine learning to be conditional on the data types shown in FIG. 7.

Figure 8:
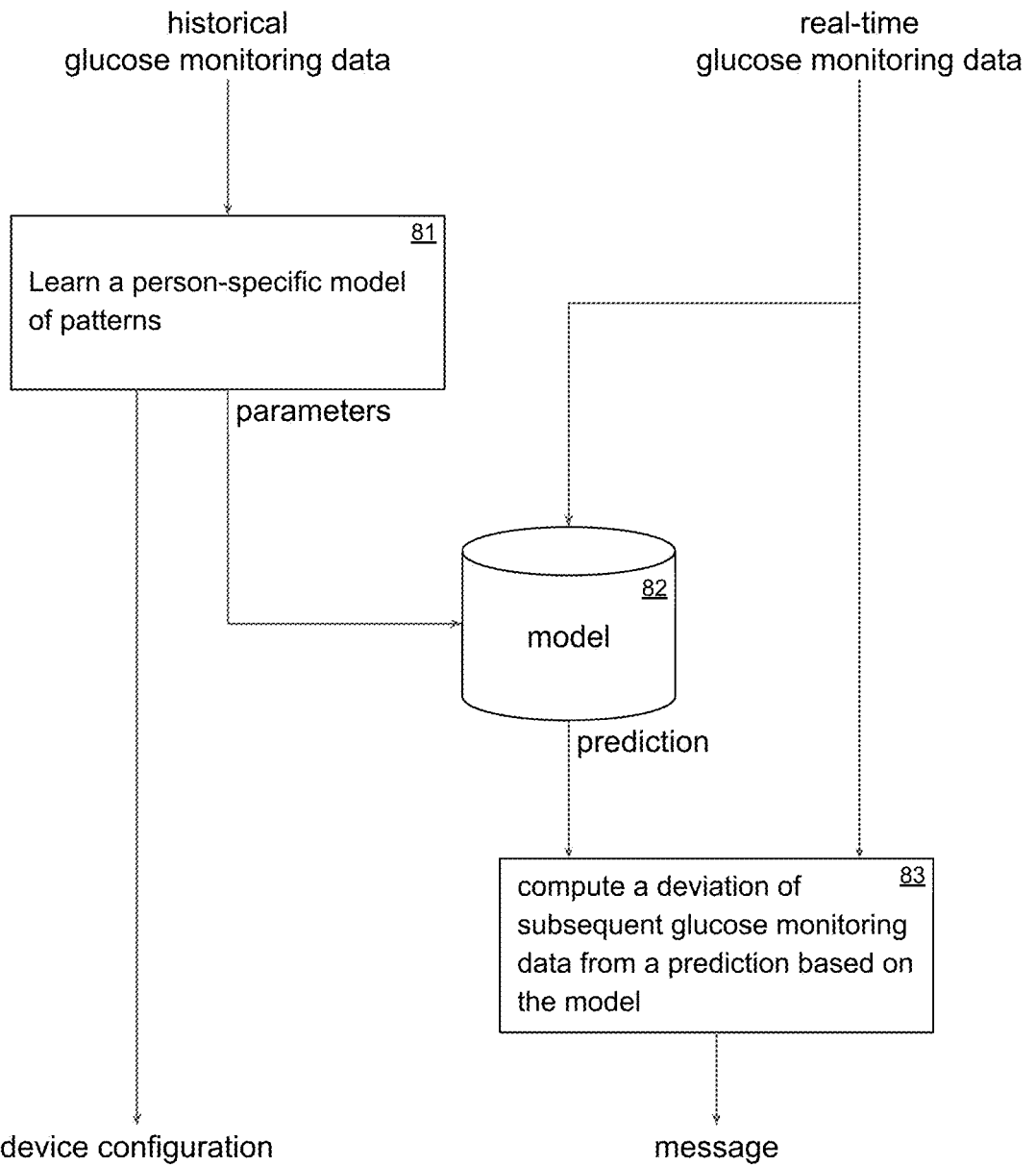
FIG. 8 is a diagram of an example of a method for reporting pathophysiologic dysglycemia.

FIG. 8 is a diagram of another example method for reporting pathophysiologic dysglycemia. It receives historical glucose monitoring data for a specific person and uses the data as input to a training process 81. The training produces parameters for a model 82 that can predict patterns for real-time glycemia. The model 82 can be applied in real-time to glucose monitoring data from the person. The model can also, in some implementations, use the person's risk factors and additional real-time data for the person.

Subsequently to receiving the training data for the model, the method of FIG. 8 received real-time glucose monitoring data. The model 82 predicts patterns of glycemia levels. That can be compared, in real-time to the real-time monitoring data to compute a deviation 83 of the actual real-time glycemia levels from the predicted glycemia levels. The level of deviation can be reported directly to the person or their QHP. Alternatively or additionally, the deviation can be translated to derived predictions or alerts.

Aside from the predictions described above with respect to FIG. 6, the deviations can be used to produce warnings or alerts. Whereas some conventional systems give alerts when a user approaches a condition of dysglycemia, that can have unnecessary false alarms. False alarms cause users to develop a habit of ignoring alarms. By conditioning the alarm on a model of expected patterns of glycemia, the implementation of FIG. 8 provides for more accurate compliance of patents and early warning of actual, serious, recent onset of or clinically meaningful progression in trends toward conditions of dysglycemia and related complications.

An additional feature of the example implementation of FIG. 8 is that the process of learning a person-specific model of patterns of glycemia can also produce parameters and models that can be used to configure devices such as CGM diagnostic devices and insulin pump therapeutic devices.

Figure 9:
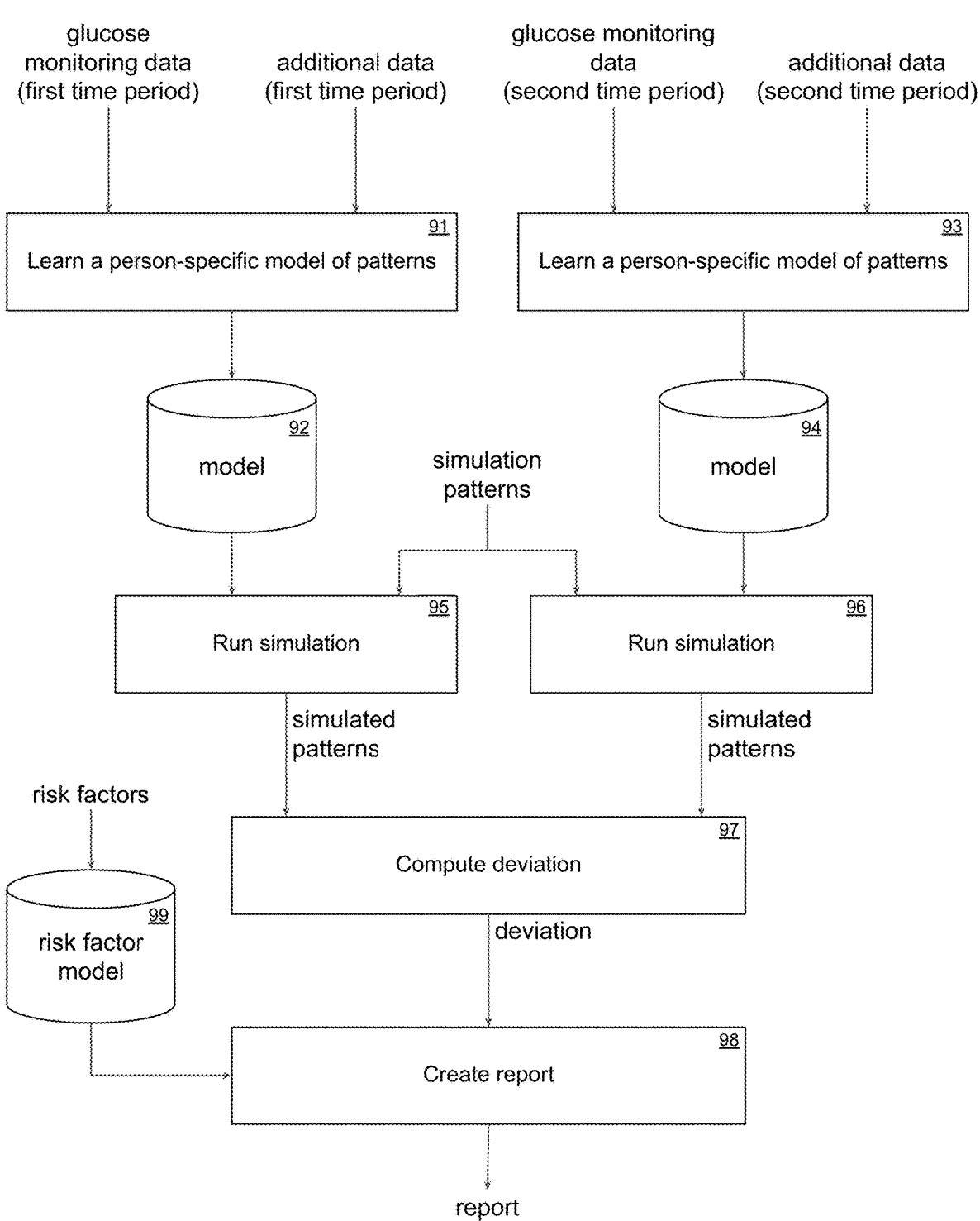
FIG. 9 is a diagram of an example of a method for reporting pathophysiologic dysglycemia.

FIG. 9 is a diagram of another example of a method for reporting pathophysiologic dysglycemia. It includes a step 91 of training a machine-learned model 92 to predict patterns of glycemia from additional data captured during the same time period as the glucose monitoring training data. The method includes a similar step 93 of training a machine-learned model 94 to predict patterns of glycemia from person-specific glucose monitoring data and additional data from a second time period that is different from the first time period.

In general, the accuracy of the first trained model 92 and second trained model 94 are higher if trained with more data. To train with enough data for a clinically dependable prediction accuracy would require, in some implementations, data collected for a duration of at least 1 month or 30 days. Assuming 3 meals per day, that gives about 90 examples of peaks and decays of glycemia and, also, will span the occurrence of many other events which are factors in glycemia, such as strenuous exercise which might occur irregularly or an occasional span of a few meals all of which are low in carbohydrates. More data is generally preferable.

To accurately recognize pathophysiologic changes requires that the person-specific models be trained over sufficient durations and compared to/contrasted with other such durations starting at sufficiently different time periods as to be able to detect a trend in the person's body's pathophysiologic glycemic state amid the noise of meal-to-meal and other differences that result from dynamic factors such as amount of exercise and sugar consumption. In general, a longer spacing between the time periods used for training the person-specific models, the more accurate the detection of trends will be. However, it is helpful if the spacing is short enough to detect trends before a chronic condition of pathophysiologic dysglycemia results in dangerous levels of dysglycemia, DKA, or other "interval" events, thus enabling preventative intervention. If the second time period of data used to train the second model begins at least 3 months or 90 days after the first time period of data used to train the first model, that is sufficient for some implementations to have clinically meaningful accuracy. Longer time periods for both CGM data and spacing between model training periods improves accuracy.

Various types of additional data can be used for various implementations. Some examples are time of meals (logged or captured by sensors such as glasses with cameras an object recognition image processing algorithm), contents of meals (logged or captured similarly), body movement such as number or frequency of steps, heart rate, blood oxygen concentration, blood pressure, body temperature, ambient temperature, sleep patterns, and neural activity, or the results of other diagnostic testing, such as Aby tests and the duration since they became positive. In various implementations, such types of additional data can be captured by body-worn devices, captured by adjacent devices, logged manually by users, or accessed from other databases, e.g. via API from EHRs. The capture of the additional data is especially useful if captured concurrently with the glucose monitoring data. The concurrent capture of additional data can be instantaneously sampled with glycemia data or captured one or more times during a period of capturing the related glycemia data.

Well-trained models can predict patterns of glycemia with high accuracy for any given pattern of additional data. Industry standard simulation patterns of the additional data may be agreed to give most accurate diagnoses. Some simulation patterns might test large deviations in dietary sugar intake, large deviations in exercise regimens, or long-term averages.

For a given simulation pattern, the method runs the first model 92 with the simulation pattern in steps 95 and runs the second model 96 on the simulation pattern in step 96 to produce simulated patterns of glycemia. A further step 97 computes a deviation in the simulated patterns. The deviations can be used for a step of creating a report 98 as described with respect to the examples of FIG. 5 and FIG. 6.

The report creation 98 can also be conditioned on risk factor parameters. A model of risk factor parameters 99 can be trained from data across a large population. Applying the risk factor model 99 to the person-specific risk factor produces parameters that can be used to condition the report creation 98. Accordingly, an accurate person-specific report is produced that a QHP, patient, or their caretaker can use to develop a care plan.

Variations in the Population

Some implementations include models of large populations in conjunction with person-specific models. The risk factor model 99 of FIG. 9 is one example of a population-wide model, and the pre-trained model 61 of FIG. 6 is another. Such models can, in various implementations, be trained using a corpus of real world evidence (RWE) associated with medical diagnoses. Such corpora are available within some private health systems such as Kaiser Permanente or national health systems such as the British National Health Service (NHS).

Generally, machine learned model accuracy improves with more training data (assuming a consistent statistical distribution). Such corpora can grow over time, and training enhanced to create ever more accurate models. The training of a person-specific model for glycemia patterns may be more efficient if the learning from an individual person's CGM data begins with a pre-trained model.

It can be helpful for training if the corpus of medical data is labeled with attributes of the subject person including one or more of age, antibody test status (if known), time since the Aby test became positive, OGTT test results (if known), genetic risk factors (if known), and other risk factors. A well labeled corpus enables a model to be trained that is easily made conditional based on labeled attributes of the data. Results can be filtered by conditional labels. But models of statistical regression can also be used with non-binary label values for attributes such as average heart rate and estimated sugar intake with meals.

Risk Factors

Human leukocyte antigen (HLA) proteins are part of the major histocompatibility complex (MHC) proteins coded on human chromosome 6. The HLAs encode cell surface proteins that regulate the immune system. Mutations in the HLA coding segments of DNA are known to cause type 1 diabetes and some other autoimmune diseases. Mutations in HLA-DR3 and HLA-DR4 are relatively common in people with European descendants. Mutations in HLA-DR7 are relatively common in people with African descendants. Mutations in HLA-DR9 are relatively common in people with Japanese descendants. Personal genome sequencing can detect, with high certainty, whether a person has such mutations or not, which is a binary risk factor. HLA mutations can be detected from gene sequencing around birth, any time afterwards, and even in utero.

The presence, absence, or unknown state of HLA mutations can be input factors to a statistical model trained to predict likelihood and severity of type 1 diabetes. Such models can be trained from corpora of records of type 1 diabetes symptoms and gene mutations across large populations.

Other yet unidentified genetic mutations may also cause or create a predisposition to type 1 diabetes. Such mutations may also be used in such a model.

Some other risk factors can be measured as non-binary levels. For example, behavioral and dynamic risk factors such as measured or estimated amounts of different types of sugars and other carbohydrates eaten, percent body fat, co-morbidities like polycystic ovarian syndrome, amount of exercise as identifiable through heart rate or step count, and length of time spent logged in to devices having their screens turned on.

Other risk factors useful for training conditional models include data from other body-worn or implanted sensors such as meal type recognition by logging or camera image processing, timing of meals, blood oxygen concentration, blood pressure, body temperature, ambient temperature, sleep patterns, and neural activity.

Standard of Care

Figure 10:
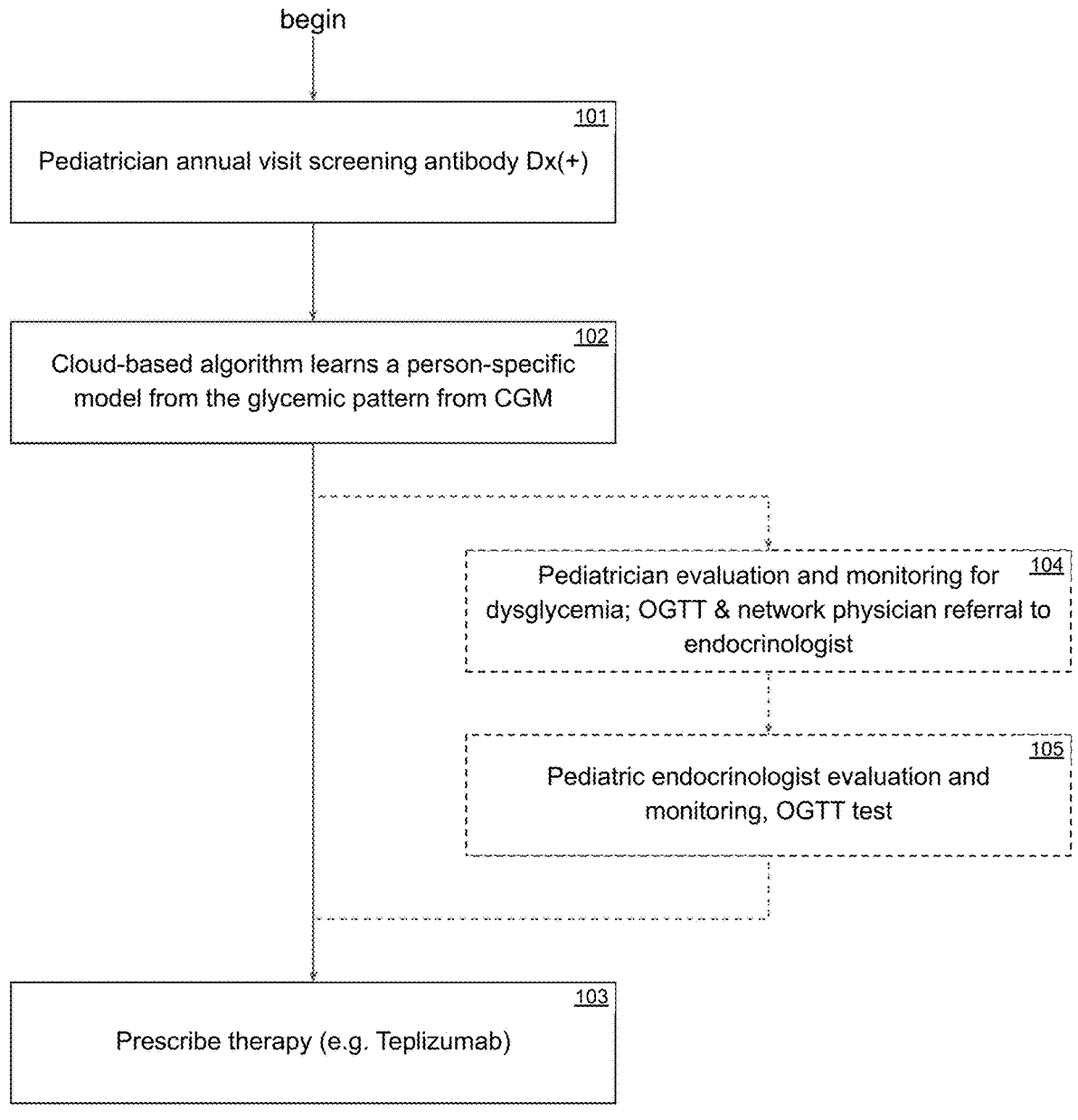
FIG. 10 shows examples of standard of care pathways.

Various implementations of methods disclosed here enable a new standard of care and care pathway for type 1 diabetes patients. FIG. 10 shows a high level flowchart of one possible care pathway. As an initial step 101, a doctor, such as a pediatrician, screens a patient with an antibody diagnostic (Dx) test. If the patient is Aby+, the doctor may recommend or prescribe CGM for the patient.

In the next step of the care pathway 102, the CGM device uploads test information to a cloud based server. The server uses a multiplicity of CGM glycemia samples, and potentially additional information, to train a patient-specific model of patterns of glycemia. In particular, some trained models predict the patient's glycemic response to meals. The cloud server can also use real-time CGM readings of glycemia to recognize dysglycemia and alert a physician such as a pediatrician or other QHP.

Finally, in a further step 103, in response to a model predicting pathophysiologic dysglycemia, the QHP can prescribe a therapy such as a prescription to the pharmaceutical therapeutic Teplizumab. The prescription step can be done, even if few or no incidents of acute dysglycemia have occurred. This can prevent DKA, long before it would occur under other standards of care.

Under an alternative standard of care, the patient care pathway might include, upon a cloud-based prediction of pathophysiologic dysglycemia, a step 104 of a physician, such as a pediatrician, a primary care physician, or general practitioner evaluating and monitoring the patient. The evaluation may include an OGTT. Depending on the results of the evaluation and monitoring, the physician may refer the patient to a specialist such as an endocrinologist. The choice of endocrinologist may involve selecting from one or more endocrinologists participating within a physician network.

In an additional step 105, the endocrinologist performs additional evaluations and monitoring. This may include an OGTT, genetic testing, or other screening. The endocrinologist may then prescribe a therapy step 103 such as a prescription for Teplizumab.

Under one such standard of care, the initial physician or endocrinologist, for patients without antibodies to insulin-producing pancreatic beta cells, might order an OGTT and order tests for antibodies to pancreatic beta cells. For patients with two or more antibodies to insulin-producing pancreatic beta cells, either physician might order an OGTT and, if positive, diagnose Type1 Diabetes, Stage 2 and intervene directly with a disease-modifying, preventative therapeutic.

FIG. 11 shows an example of a standard of care pathway using detection of deviation, interpretation, and a conclusion of diagnosis and recommended intervention. As an initial step 111, a doctor, such as a pediatrician, screens a patient with an antibody diagnostic (Dx) test. If the patient is Aby+, the doctor may recommend or prescribe CGM for the patient.

In the next step of the care pathway 112, the CGM device uploads test information to a cloud based server. The server uses a multiplicity of CGM glycemia samples, and potentially additional information, to train a patient-specific model of patterns of glycemia. In particular, some trained models predict the patient's glycemic response to meals. The cloud server can also use real-time CGM readings of glycemia to recognize dysglycemia and alert a physician such as a pediatrician or other QHP.

In a further step 113, an algorithm on the cloud server compares subsequent CGM data to a pattern predicted by the trained model to detect the presence or measure the amount of deviation between the measured data and the predicted pattern. In a further step 114, an algorithm interprets the clinical meaningfulness of the deviation. In a further step 115, an algorithm draws a conclusion from the interpretation. The conclusion could be, for example, that there is no disease detected or that the person has type 1 diabetes at stage 2.

Finally, in a further step 116, an algorithm recommends an intervention. The recommended intervention can be selected from a set of rules based on the measured data. The rule might include non-binary information, such as a dosage level for a preventative pharmaceutical treatment.

With data sufficient to warrant decisions by a prudent physician in a person's care pathway showing detection of the transition over time from a state of euglycemia to a state of dysglycemia based on patterns from a learned model may be used for the care pathways described above.

Under other standards of care, it is possible to perform screening and testing in an alternative order. Specifically, that is by inverting Aby and CGM. When the AICGM is performed in someone already known to be Aby+, the dysglycemia meets the criteria for diagnosis of Type I Diabetes, Stage 2 (TIDS2), in which case therapeutic intervention is warranted. Additionally, in some new standards of care, AICGM supplants the conventional standard of care, which is OGTT (Oral Glucose Tolerance Testing).

Another standard of care computes a tripartite likelihood/confidence score from the model, such that, for patients with lower scores, physicians simply continue on the AICGM. For middle scores, patients are sent for OGTT, and patients with upper scores get therapeutic prescriptions directly.

As described above, early recognition of pathophysiologic dysglycemia can be used asynchronously or synchronously with evaluation and management. Recognizing pathophysiologic trends recognizes progression toward stages of diabetes which approach a threshold at which the pathophysiologic state might warrant preventive intervention An additional benefit of the new standards of care enabled by early recognition of pathophysiologic dysglycemia is to delay insulin deficiency associated with stages of diabetes. This is an improvement over therapeutic intervention by replacing insulin or administering metformin to enhance insulin responsiveness.

Additional Remarks

Many of the methods and devices described in this specification are implemented using computer processors and digital memory devices that store software instructions that, when executed by one or more processors, implement the methods and functions described. The computer processors may be central processing units (CPU), graphics processing units (GPU), digital signal processors (DSP), or others. Such processors are typically implemented in chips such as system-on-chip (SoC) devices or field programmable gate arrays (FPGA). Some chips or chip packages comprise both computer processors and the digital memory, though other implementations have separate processor and memory chips.

This specification gives many examples. Various practical implementations will include combinations of features described in different examples. Furthermore, it should be understood that some implementations omit features shown in examples that are not essential to the functions described. Some implementations use multiple instances of features shown or described where doing so does not interfere with the functions described.

The invention claimed is:

1. A computer-implemented method of detecting early stage diabetes to identify an opportunity for early preventative disease-modifying therapy, the method comprising:

during a first time period, the first time period being long enough for at least several occasions between states of euglycemia and dysglycemia:

configuring a glucose sensor to sample first glucose monitoring data for a person at a first sampling frequency equal to or higher than a transition frequency of transitions between the state of euglycemia and the state of dysglycemia, the person being antibody positive (Aby+);

receiving at a remote server the first glucose monitoring data;

configuring a second sensor to obtain first additional person-specific data for the person at least at the first sampling frequency, the first additional person-specific data including one or more types of additional biometric data or activity data of the person;

receiving at the remote server the first additional person-specific data;

receiving at the remote server first food data including first foods eaten during the first time period and first associated times of day;

during each of one or more second time periods, the one or more second time periods initiating a duration after the first time period, each of the one or more second time periods being long enough for at least several occasions between the states of euglycemia and dysglycemia:

configuring the glucose sensor to sample second glucose monitoring data for the person at a second sampling frequency equal to or higher than the transition frequency of transitions between the state of euglycemia and the state of dysglycemia;

receiving at the remote server the second glucose monitoring data;

configuring the second sensor to obtain second additional person-specific data for the person at least at the first sampling frequency, the second additional person-specific data including the one or more types of additional biometric data or activity data of the person;

receiving at the remote server the second additional person-specific data;

receiving at the remote server second food data including second foods eaten during the second time period and second associated times of day;

using statistical analysis to generate a first person-specific model of first patterns in the first glucose monitoring data in relation to the first food data and the first additional person-specific data for the first time period;

using statistical analysis to generate in real time respectively one or more second person-specific models of second patterns in the second glucose monitoring data in relation to the second food data and the second additional person-specific data for the one or more second time periods;

using third food data, third additional person-specific data and the first person-specific model to generate a first simulated glucose pattern for the person based on the first time period;

using the third food data, the third additional person-specific data and the second person-specific model to generate in real time a second simulated pattern for the person based on at least one of the one or more second time periods;

computing in real time glucose-pattern deviation information between the first simulated pattern and the at least one of the one or more second simulated patterns for the person;

monitoring in real time the glucose-pattern deviation information for an actual diabetes pathophysiologic change condition in the person indicative that early preventative disease-modifying therapy may be warranted, the actual diabetes pathophysiologic change condition generated from a machine learned model trained on glycemic data gathered from at least a set of individuals in the population having similar characteristics as the person; and when the actual pathophysiologic change condition based on the glucose pattern deviation information for the person is satisfied, generating a notification in real time to at least one of the person, a caregiver or a healthcare provider that early preventative disease-modifying therapy may be warranted.

2. The method of claim 1 wherein the notification includes a probability of a positive result from an oral glucose tolerance test, the probability computed using a population-wide model of oral glucose tolerance test results relative to computed pattern deviation information.

15

3. The method of claim 1 wherein the notification includes at least one of a diagnostic recommendation or an intervention recommendation to a remote electronic health record database via a computer network.

4. The method of claim 1 wherein computing the pattern deviation information comprises at least one of:
(a) computing a difference in amplitude; or
(b) computing a difference in rate of change.

5. The method of claim 3 further comprising obtaining an antibody test result for the person, wherein at least one of the diagnostic recommendation or the intervention recommendation is computed using a population-wide model as a function of the antibody test result.

6. The method of claim 3 wherein at least one of the diagnostic recommendation or the intervention recommendation is one or more of:
that additional diagnostic testing is warranted;
that a diagnosis of disease progression is warranted;
that a diagnosis of Type I Diabetes, Stage 2 should be considered; or
that intervention with the early preventative disease-modifying therapy may be warranted.

7. The method of claim 3 further comprising obtaining at least one of a genetic test result or a history of intervention with disease-modifying treatment for the person, wherein at least one of the diagnostic recommendation or the intervention recommendation is computed as a function of at least one of:
the genetic test result; or
the history of intervention with disease-modifying treatment.

8. The method of claim 1 performed by the remote server in response to a request through a web API.

9. The method of claim 1 wherein the glucose sensor and the second sensor are parts within a single device.

10. The method of claim 1 wherein computing the pattern deviation information comprises computing a difference in a parameter learned from the first and/or second additional patient-specific data.

11. The method of claim 1 wherein the duration is about a month.

12. The method of claim 1 wherein the first person-specific model is generated from a pre-trained population-wide model to reduce computations needed to generate the first person-specific model.

13. A non-transitory computer readable medium storing code that causes a computer to:
during a first time period, the first time period being long enough for at least several occasions between states of euglycemia and dysglycemia:
configure a glucose sensor to sample first glucose monitoring data for a person at a first sampling frequency equal to or higher than a transition frequency of transitions between the state of euglycemia and the state of dysglycemia, the person being antibody positive (Aby+);
receive at a remote server the first glucose monitoring data;
configure a second sensor to obtain first additional person-specific data for the person at least at the first sampling frequency, the first additional person-specific data including one or more types of additional biometric data or activity data of the person;
receive at the remote server the first additional person-specific data;

receive at the remote server first food data including first foods eaten during the first time period and first associated times of day;
during each of one or more second time periods, the one or more second time periods initiating a duration after the first time period, each of the one or more second time periods being long enough for at least several occasions between the states of euglycemia and dysglycemia:
configure the first glucose sensor to sample second glucose monitoring data for the person at a second sampling frequency equal to or higher than the transition frequency of transitions between the state of euglycemia and the state of dysglycemia;
receive at the remote server the second glucose monitoring data;
configure the second sensor to obtain second additional person-specific data for the person at least at the first sampling frequency, the second additional person-specific data including the one or more types of additional biometric data or activity data of the person;
receive at the remote server the second additional person-specific data;
receive at the remote server second food data including second foods eaten during the second time period and second associated times of day;
use statistical analysis to generate a first person-specific model of first patterns in the first glucose monitoring data in relation to the first food data and the first additional person-specific data for the first time period;
use statistical analysis to generate in real time respectively one or more second person-specific models of second patterns in the second glucose monitoring data in relation to the second food data and the second additional person-specific data for the one or more second time periods;
use third food data, third additional person-specific data and the first person-specific model to generate a first simulated glucose pattern for the person based on the first time period;
use the third food data, the third additional person-specific data and the second person-specific model to generate in real time a second simulated pattern for the person based on at least one of the one or more second time periods in real time;
compute in real time glucose-pattern deviation information between the first simulated pattern and the at least one of the one or more second simulated patterns for the person;
monitor in real time the glucose-pattern deviation information for an actual diabetes pathophysiologic change condition in the person indicative that early preventative disease-modifying therapy may be warranted, the actual diabetes pathophysiologic change condition generated from a machine learned model trained on glycemic data gathered from at least a set of individuals in the population having similar characteristics as the person; and
when the actual pathophysiologic change condition based on the glucose pattern deviation information for the person is satisfied, generate a notification in real time to at least one of the person, a caregiver or a healthcare provider that early preventative disease-modifying therapy may be warranted.

14. The computer readable medium of claim 13 wherein the notification includes a probability of a positive result from an oral glucose tolerance test, the probability computed using a population-wide model of oral glucose tolerance test results relative to computed pattern deviation information.

15. The computer readable medium of claim 13 wherein the notification includes at least one of a diagnostic recommendation or an intervention recommendation to a remote electronic health record database via a computer network.

16. The computer readable medium of claim 13 wherein the pattern deviation information is computed by one of
(a) computing a difference in amplitude; or
(b) computing a difference in rate of change.

17. The computer readable medium of claim 15 that further causes the computer to obtain at least one of a history of prior intervention with disease-modifying treatment or an antibody test result for the person, wherein at least one of the diagnostic recommendation or the intervention recommendation is computed as a function of at least one of:
the antibody test result; or
the history of prior intervention with disease-modifying treatment.

18. The computer readable medium of claim 15 wherein at least one of the diagnostic recommendation or the intervention recommendation is one or more of:
that additional diagnostic testing is warranted;
that a diagnosis of disease progression is warranted;
that a diagnosis of Type I Diabetes, Stage 2 should be considered; or
that intervention with a preventative disease-modifying therapy may be warranted.

19. The computer readable medium of claim 15 that further causes the computer to obtain at least one of:
a genetic test result; or
a history of intervention with disease-modifying treatment for the person, wherein at least one of the diagnostic recommendation and the intervention recommendation is computed as a function of at least one of:
the genetic test result; or
the history of intervention with disease-modifying treatment.

20. The computer readable medium of claim 13 wherein the obtaining is performed by the remote server in response to a request through a web API.

21. The computer readable medium of claim 13 wherein the glucose sensor and the second sensor are parts within a single device.

22. The computer readable medium of claim 13 wherein computing the pattern deviation information comprises computing a difference in a parameter learned from the first and/or second additional patient-specific data.

23. The computer readable medium of claim 13 wherein the duration is about a month.

24. The computer readable medium of claim 13 wherein the first person-specific model is generated from a pre-trained population-wide model to reduce computations needed to generate the first person-specific model.

* * * * *